United States Patent [19]
Kobren et al.

[11] Patent Number: 6,083,177
[45] Date of Patent: *Jul. 4, 2000

[54] CERVICAL BIOPSY DEVICE AND METHOD

[76] Inventors: Myles S. Kobren, 100 Manetto Hill Rd. - Suite 302, Plainview, N.Y. 11803; Staci L. Kobren, 18 The Grasslands, Woodbury, N.Y. 11797; Joseph C. Segen, 1 Hawthorne La., Manhasset, N.Y. 11030

[ * ] Notice: This patent is subject to a terminal disclaimer.

[21] Appl. No.: 09/144,226

[22] Filed: Aug. 31, 1998

Related U.S. Application Data

[63] Continuation-in-part of application No. 08/528,249, Sep. 14, 1995, Pat. No. 5,611,352, and application No. 08/778,606, Jan. 6, 1997, Pat. No. 5,800,362.

[51] Int. Cl.⁷ .................................................. A61B 10/00
[52] U.S. Cl. ........................ 600/564; 604/170; 606/172
[58] Field of Search .................................... 600/562, 564, 600/566, 567; 604/157, 117; 606/167, 170, 172

[56] References Cited

U.S. PATENT DOCUMENTS

| | | | |
|---|---|---|---|
| 4,667,684 | 5/1987 | Leigh | 600/567 |
| 4,733,671 | 3/1988 | Mehl | 600/567 |
| 5,368,046 | 11/1994 | Scarfone et al. | 604/117 |

*Primary Examiner*—Max Hindenburg
*Assistant Examiner*—Pamela L. Wingood
*Attorney, Agent, or Firm*—Eliot S. Gerber

[57] ABSTRACT

An instrument and method for the biopsy of cervical tissue samples uses a needle-stylet having a sharp tip and a tissue sample cradle. A sheath surrounds the stylet and is advanced to sever tissue. A barrier disk on the sheath limits its penetration into the tissue.

1 Claim, 10 Drawing Sheets

CERVICAL BIOPSY DEVICE AND METHOD

RELATED APPLICATIONS

This application is a continuation-in-part application partly based on application Ser. No. 08/528,249, filed Sep. 14, 1995, now U.S. Pat. No. 5,611,352; and application Ser. No. 08/778,606, filed Jan. 6, 1997, now U.S. Pat. No. 5,800,362.

FIELD OF THE INVENTION

The present invention is directed to a biopsy device for obtaining cervical tissue samples and more particularly to a disposable cervical biopsy needle.

BACKGROUND OF THE INVENTION

The extraction and analysis of tissue samples has proven a highly effective procedure for identifying cancer, pre-malignant conditions and other infections. This procedure has proven particularly effective for identifying pre-invasive cervical lesions, the treatment of which is usually highly successful.

Before using a biopsy device to extract and analyze cervical tissue, a doctor will typically conduct an initial screening procedure known as a Pap smear. This screening procedure involves rotating a swab, cytobrush or spatula along the portio cervix or vaginal mucosa to obtain a cell sample which is then spread on a clear slide and analyzed. If the cells appear atypical with dysplastic features, or reflect low-grade or high-grade intraepithelium lesions, then a tissue biopsy is usually required.

The most common biopsy device currently used for cervical tissue extraction is a punch biopsy. In order to obtain a tissue sample, a practitioner observes the tissue through a colposcope, which magnifies the tissue, and then uses the punch biopsy to grasp a portion of tissue and extract it. Major drawbacks of the punch biopsy are that it may cause tissue trauma, disfigurement of the cervix and significant pain. Further, the difficulty in simultaneously using two separate instruments, i.e., viewing the tissue through the colposcope while trying to manipulate the punch biopsy, often results in an inadequate specimen. As a result, practitioners often grasp a larger portion of the tissue than necessary to ensure that an adequate specimen is retrieved. This may result in excessive bleeding requiring cauterization.

U.S. Pat. No. 4,461,305, herein incorporated by reference, discloses a biopsy device comprising a generally cylindrical core-cutter with a rotatably mounted cutting blade. A plunger, slidably mounted within the core-cutter, is used to limit the depth to which the core cutter advances into the tissue to thereby provide greater control over the sample size. The plunger also provides a means to eject the severed sample. However, it is still possible for the device to penetrate excessively into the tissue.

U.S. Pat. No. 4,976,269 to Mehl, herein incorporated by reference, discloses a tissue needle for extracting a biopsy sample having a stylet, with a sharp tip, a cavity (sample notch) near the tip, a tubular cannula which is spring loaded, and a trigger in a handle. It does not show any means to limit the depth of penetration of the stylet or cannula into tissue.

In addition, the foregoing devices are designed for reuse, which is a major drawback in today's society where the use of contaminated needles has significantly contributed to the spread of diseases.

Accordingly, the need exists to provide an improved device and method for obtaining tissue samples which reduces the amount of pain and bleeding experienced by a patient.

SUMMARY OF THE INVENTION

Thus, it is a purpose of the present invention to overcome the disadvantages of the prior art and thereby provide a biopsy device and method of use therefore for performing cervical biopsies which eliminates the need to use a colposcope and prevents excessive penetration into tissue.

In accordance with a preferred embodiment, the biopsy device includes a needle associated with a handle. The needle includes a stylet having a sharp tip for insertion into tissue. The stylet has a cradle (cavity or sample notch) in an outer surface for collecting a tissue specimen. The needle further includes a sheath (tubular cannula) surrounding a portion of the stylet and movable with respect thereto. The sheath has a cutting edge for cutting tissue and filling the cradle with a tissue specimen. A limiting disc positioned on the sheath acts as a barrier to prevent excessive penetration into the tissue.

In a preferred embodiment, at least the components of the needle, i.e., the stylet, sheath and limiting disc, comprise a disposable unit which is attachable to the handle and packaged separately therefrom. The handle preferably has a pistol-type configuration in which a grip portion is pivotally attached to the housing. Thus, the grip portion may be locked in place at different angles with respect to the needle which is attached to the housing.

It is, therefore, an object of the present invention to provide a biopsy device which includes a limiting disc which acts as a barrier mechanism to prevent excessive tissue penetration.

It is still another object of the invention to provide a method of performing a cervical biopsy.

These and other objects of the present invention will become apparent from the detailed description to follow.

BRIEF DESCRIPTION OF THE DRAWINGS

There follows a detailed description of the preferred embodiments of the present invention which are to be taken together with the accompanying drawings, wherein.

DESCRIPTION OF THE PREFERRED EMBODIMENTS

Referring now to the figures, like elements are represented by like numerals throughout the several views.

Figure 1:
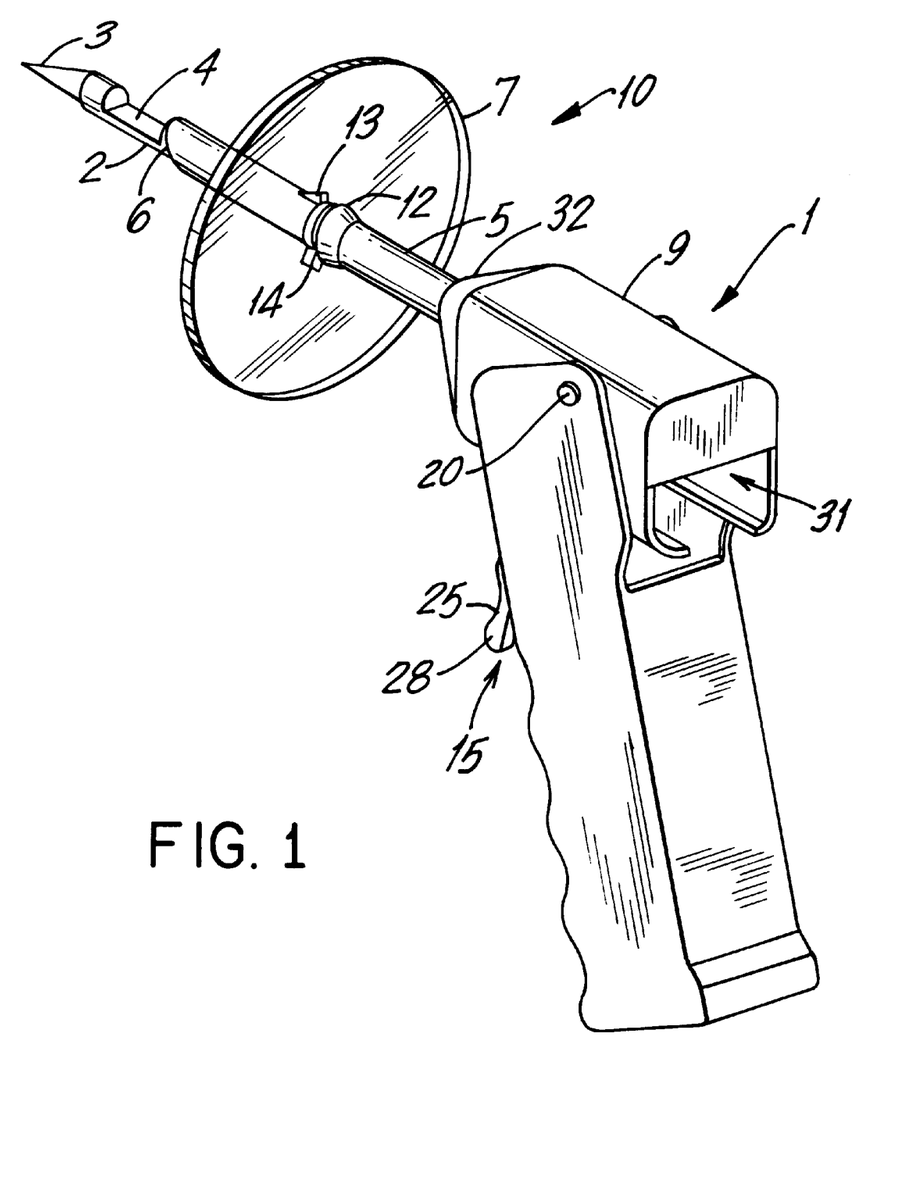
FIG. 1 shows a perspective view of the first embodiment of the biopsy device of the invention in a fully assembled form.

FIG. 1 shows one embodiment of the biopsy device of the invention in a fully assembled form and ready for use. The biopsy device includes a handle 1 (pistol style hand grip) to which a needle 10 is anchored. The needle 10 comprises a stylet 2 having a sharp tip 3 extending outward from the handle 1 for insertion into tissue. The stylet 2 has a cradle 4 (cavity or sample notch) in an outer surface between the tip 3 and handle 1 for receiving a tissue specimen. The needle 10 further includes a sheath 5 (tubular sheath or cannula)) which surrounds a portion of the stylet 2 and is movable thereon. The sheath 5 includes a cutting edge 6 for cutting a specimen from tissue. In the embodiment of FIGS. 1–6 the needle 10 also includes a transparent magnifying lens 7 positioned on the sheath 5 to allow the tissue to be observed both during insertion of the stylet 2 into the tissue and during the cutting procedure.

To use the biopsy device of the invention, the practitioner grips the handle 1 and optionally pushes the sheath 5 forward so that the cutting edge 6 moves toward the tip 3 of the stylet 2. The practitioner guides the stylet 2 and sheath 5 into the tissue using the magnifying lens 7 to insure that the stylet 2 is inserted properly. The practitioner then moves the sheath 5 in the reverse direction to expose the cradle 4 whereupon the tissue enters the cradle 4. The practitioner pushes the sheath 5 forward again so that the cutting edge 6 moves toward the tip 3 of the stylet 2. As it moves, the cutting edge 6 cuts the tissue and captures a specimen within the cradle 4. Because the magnifying lens 7 is located on the sheath 5, the practitioner can observe the entire cutting operation without the need for a colposcope or other separate magnifying means. Once an adequate specimen has been collected in the cradle 4, the practitioner then removes the stylet 2 with the sheath 5 covering the tissue in the cradle. He then removes the device from the patient and pulls back the sheath to uncover and remove the tissue sample from the cradle.

Figure 2:
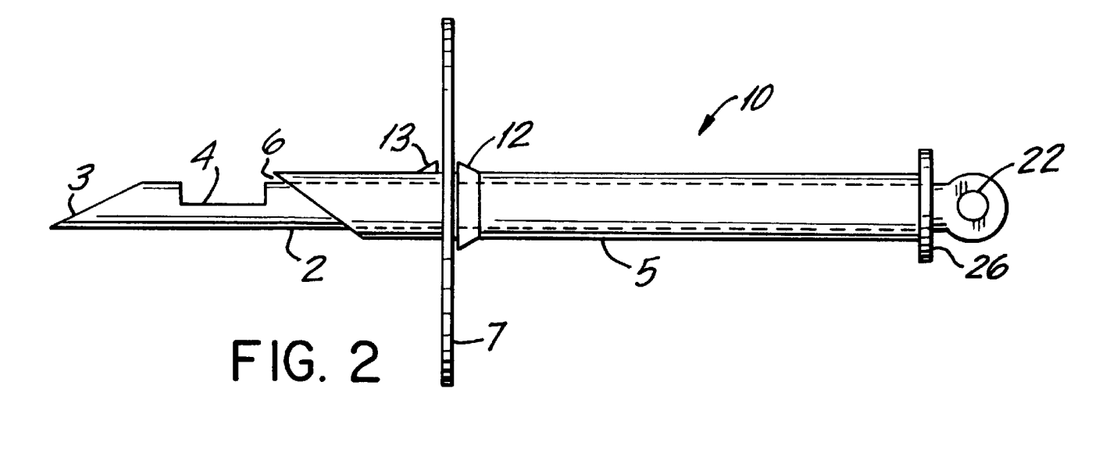
FIG. 2 shows a side view of the biopsy needle of the invention.

Because the various components of the needle 10, i.e., the stylet 2, sheath 5 and magnifying lens 7, contact the tissue during use, it is desirable that these components be separable from the handle 1 for ease in cleaning. Alternatively, one or more of these components may be disposable. Most preferably, however, the stylet 2, sheath 5 and magnifying lens 7 are packaged as a single, sterile, disposable unit as shown in FIG. 2, i.e., a unit designed for a single use. This ensures complete sterility of the components before each use. In addition, the stylet 2, sheath 5 and magnifying lens 7 can be constructed from relatively low cost materials since they are only intended to last for a single use. The magnifying lens 7, for example, need only be constructed from an inexpensive plastic that provides two to three times magnification.

Even if the stylet 2, sheath 5 and magnifying lens 7 are packaged as a single unit, it is desirable that these individual components be separable to allow greater flexibility when using the biopsy device. For example, when preparing to insert the stylet 2 and sheath 5 into tissue, the practitioner may find that stronger magnification is required. He can then quickly remove the magnifying lens 7 and replace it with a lens having greater magnification.

Figure 3:
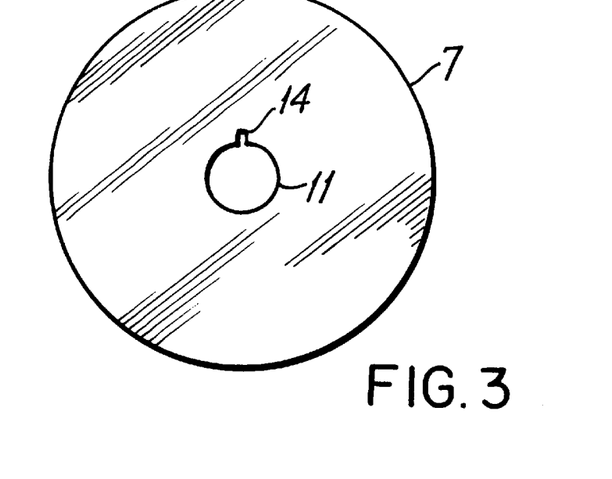
FIG. 3 shows a front view of the magnifying lens.

As shown in FIG. 3, the magnifying lens 7 is in the shape of a circular disk having a central circular opening 11 which is slightly greater in diameter than the sheath 5 The magnifying lens 7 slides over the sheath 5, which has a cylindrical shape, and is held in place between two fixed, raised sections or flanges 12,13 extending radially outward from the outer wall of the sheath 5. as shown in FIG. 2. In order to position the magnifying lens 7 between the two flanges 12,13, the central circular opening 11 includes a notch 14 which allows the magnifying lens to slide over flange 13 when notch 14 and flange 13 are aligned. Once in place, the magnifying lens 7 is rotated so that the notch 14 is out of alignment with flange 13 and is thereby held in place between the two flanges 12,13. Of course, other appropriate configurations for the magnifying glass are considered within the scope of this invention.

Figure 6:
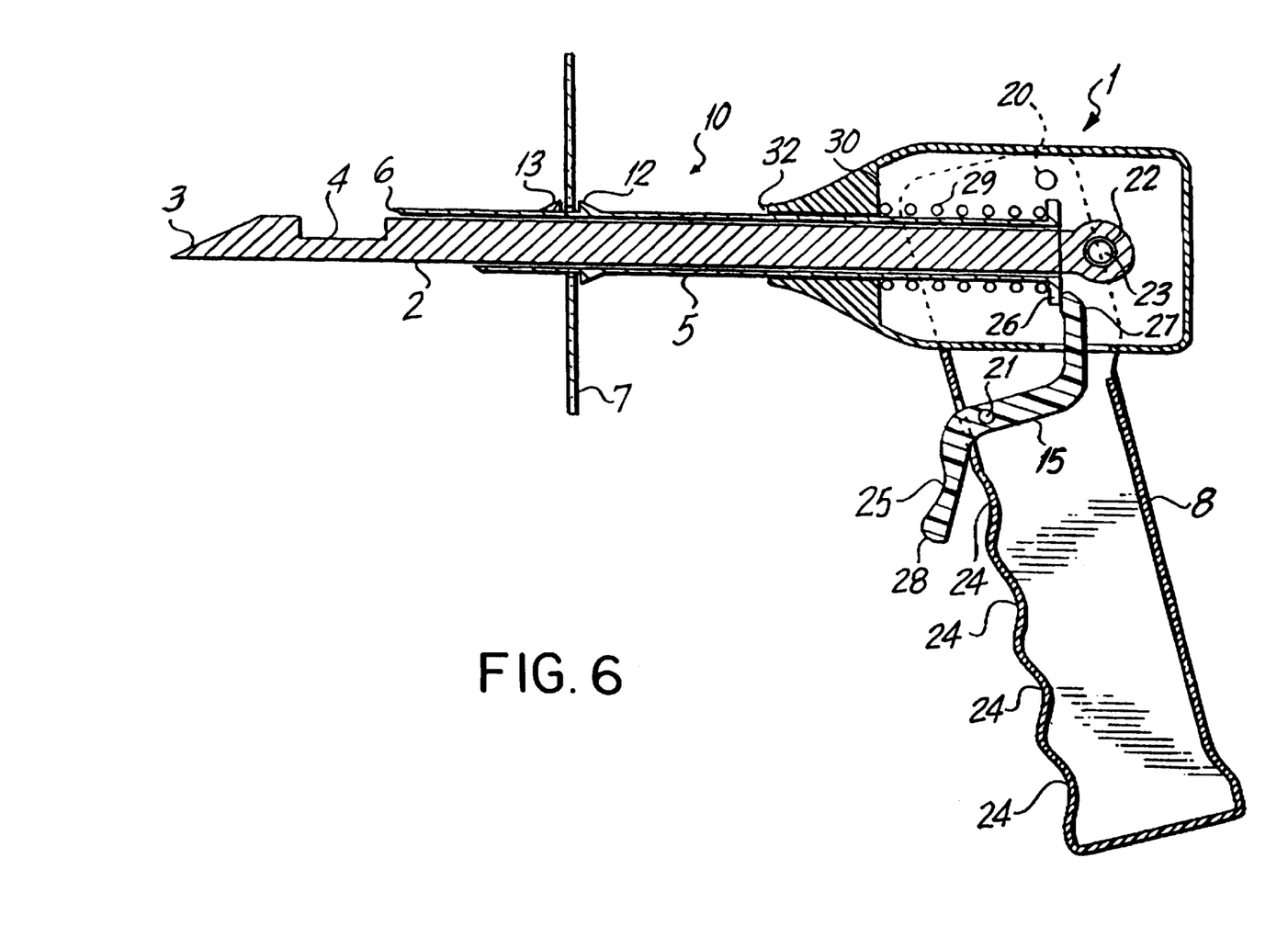
FIG. 6 shows a side cross-sectional view of the biopsy device of the invention taken along the central longitudinal axis of the needle.

Although the size of the components of the biopsy device of the invention, as well as their positioning with respect to one another, may vary considerably, it has been found that an adequate specimen may be obtained using a cradle length of about 0.4 to 0.7 centimeters, the thickness of the stylet 2 being approximately 0.25 centimeters, while the outer diameter of the sheath is 0.35 to 0.45 centimeters. The full length of that portion of the stylet 2 which extends outside of the handle 1 is about 5.0 to 8.0 centimeters, with the total combined length of the tip and cradle 4 being less than or equal to 1.5 centimeters. When the cradle 4 is exposed, the magnifying glass 4 should be positioned at about a distance of 1.7 centimeters from the tip 3 of the stylet 2. Thus, the sheath 5 must be positioned on the stylet 2 such that the distance from the far end of the tip 3 to the cutting edge 6 of the sheath is at least 1.5 centimeters, but slightly less than 1.7 centimeters, when the cradle 4 is exposed. The tip 3 and cutting edge 6 should be scalpel sharp. The opposite end of the stylet 2 includes anchoring means for attachment to the handle 1. As shown in FIGS. 2 and 6 (discussed in greater detail below), the anchoring means may be an eyelet 22 through which a rod 23 in the handle 1 extends. Alternatively, the eyelet 22 may be replaced with a hook (not shown) which hooks onto the rod 23.

The handle 1 may be constructed from a higher quality material which is designed to last for multiple uses. The same handle can then be utilized with different stylet sizes or a stronger magnifying lens. Alternatively, the handle 1 may be disposable and packaged either separately or together with one or more of the stylet 2, sheath 5 and magnifying lens 7, such that the entire biopsy device is disposable.

Although the handle 1 may have any number of configurations, a pistol-type configuration, as shown in the figures, has generally proven the most comfortable and easiest to operate with a single hand, leaving the practitioner's other hand free to enable external manipulation or provide other support. The pistol-type configuration includes a grip portion 8 attached to a housing 9 to which the needle 10 is attached. The grip portion 8 may further include grooves 24 where the practitioner's fingers rest. As shown in FIG. 1, the front opening of the housing 32 is typically narrowed to a diameter slightly larger in size than the outer diameter of the sheath 5, but smaller than flange 26 on the sheath (shown more clearly in FIG. 6) to prevent the sheath from sliding out of the housing 9. The rear portion of the housing 9 preferably includes an opening 31 to allow insertion of the needle 10.

Figure 4:
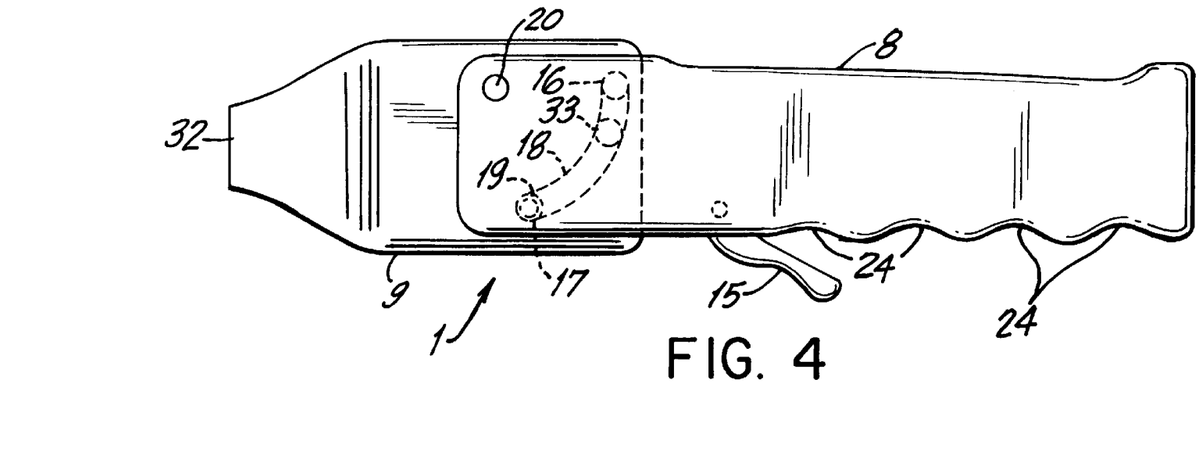
FIG. 4 shows a side view of the handle in which the grip portion is axially aligned with the housing.
Figure 5:
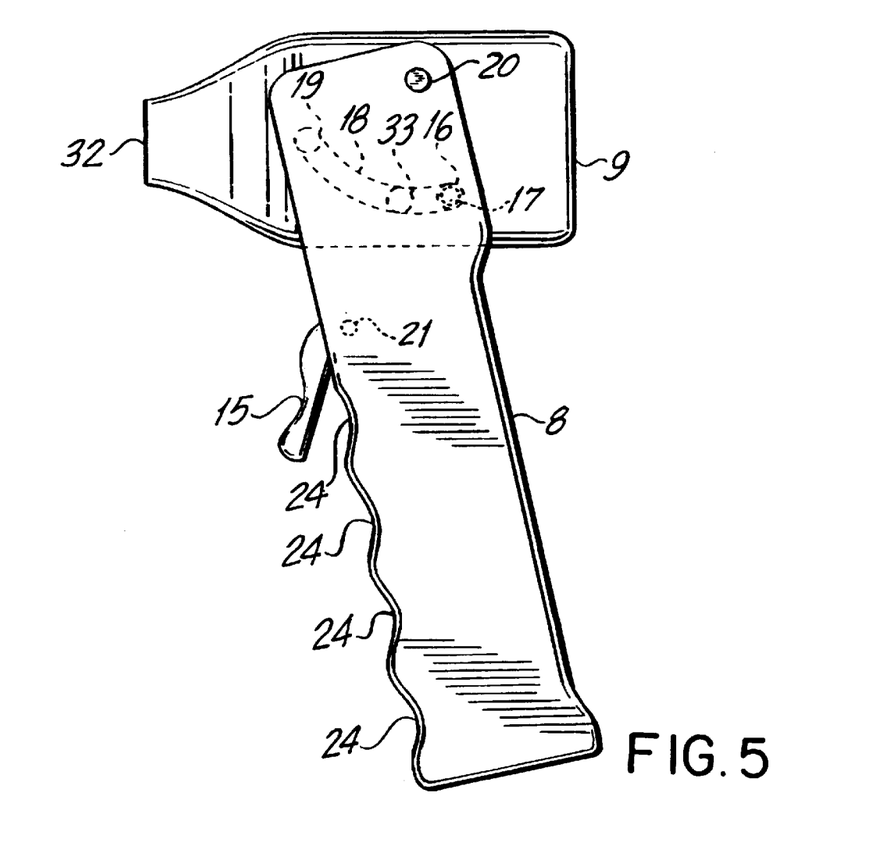
FIG. 5 shows a side view of the handle in which the grip portion is pivoted to a position in which it is almost perpendicular to the housing.

As shown in FIGS. 4 and 5, it is also desirable that the grip portion 8 of the handle 1 be pivotable with respect to the housing 9. This allows the practitioner to rotate the grip portion 8 from a position in which it is virtually perpendicular to the housing 9, shown in FIG. 5, to a position in which the grip portion 8 is linearly aligned with the housing 9, shown in FIG. 4. Although the latter position would generally not be comfortable during use, this position allows greater convenience in packaging the handle since only a narrow rectangular box is required.

The grip portion 8 pivots about a fixed point 20, which may be a rod extending through the housing 9 and grip portion 8. The grip portion 8 has an arcuate slot 18 into which at least one protrusion 17 on the housing 9 extends to guide the movement of the grip portion 8. The slot 18 includes at least one depression 16 which locks into place with the protrusion 17 on the housing 9. The housing 9 may include one or more additional protrusions 19,33 which allow the grip portion 8 to be locked into place at different angles with respect to the housing 9. Other conventional locking means may also be used for holding the grip portion 8 in place.

Although the handle 1 may include various means for moving the sheath 5 forward on the stylet 2, in a preferred embodiment, shown most clearly in FIG. 6, the means for moving the sheath 5 is a trigger 15 (squeeze trigger). A first end 28 of the trigger 15 is exposed and includes a finger engagement portion 25 which is typically engaged by the index finger of the practitioner. A second, opposite end 27 is located inside the housing 9 and rests against the flange 26 or other similar abutment at the end of the sheath 5 opposite the cutting edge 6. The trigger 15 is pivotally attached to the gripping portion 8 at a point 21 between its two ends 27,28. When the practitioner squeezes the finger engagement portion 25 of trigger 15, the end 27 presses against the flange 26 so that the sheath 5 moves toward the tip 3 of the stylet 2 and covers the cradle portion 4. When the sheath 5 moves forward, a spring 29 positioned between an interior wall 30 in the housing 9 and the flange 26 is compressed. The interior wall 30 also limits the distance that the sheath 5 is movable on the stylet 2. Upon releasing the trigger, the spring 29 returns the sheath 5 to its original position.

Figures 7, 8:
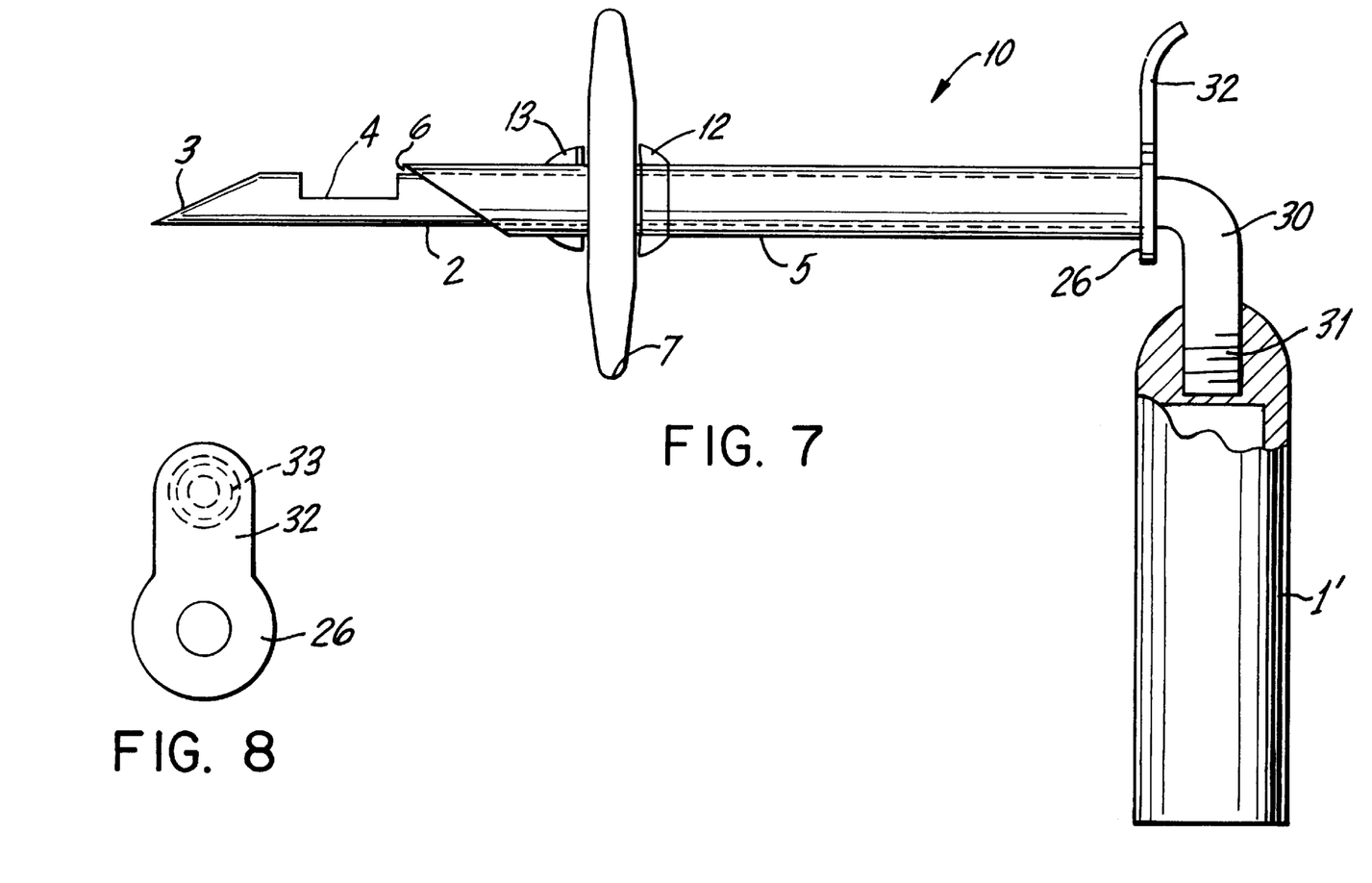
FIG. 7 shows a side cross-sectional view of another embodiment of the biopsy device of the invention taken along the central longitudinal axis of the needle.
FIG. 8 is a front view of a portion of the device of the device of FIG. 7.

In the embodiment of FIGS. 7 and 8 the stylet 2 is directly connected to a handle 1' without a trigger or spring mechanism. The proximate end of the stylet is extended with an integral portion 30 having screw threads 31. The screw threads 31 screw into a screw-threaded cavity at the top of handle 1'. The flange 26 has an integral extension portion 32 having an indentation 33. The practitioner uses one hand to grasp handle 1'. He then uses a finger to push on extension 32 to slide the cylindrical sheath 5 forward on the stylet 2. For example, the sheath is moved forward after the tip has been inserted into the wall of the cervix. The cutting edge 6 of the sheath 5 cuts the tissue sample, deposits it in the cradle 4 and covers the cradle 4 until after the device is removed from the patient. As in the prior embodiments, the magnifying lens 7 is removably mounted on sheath 5 by flange 13 and notch 14 so that the lens slides with the sheath 5.

Figure 9:
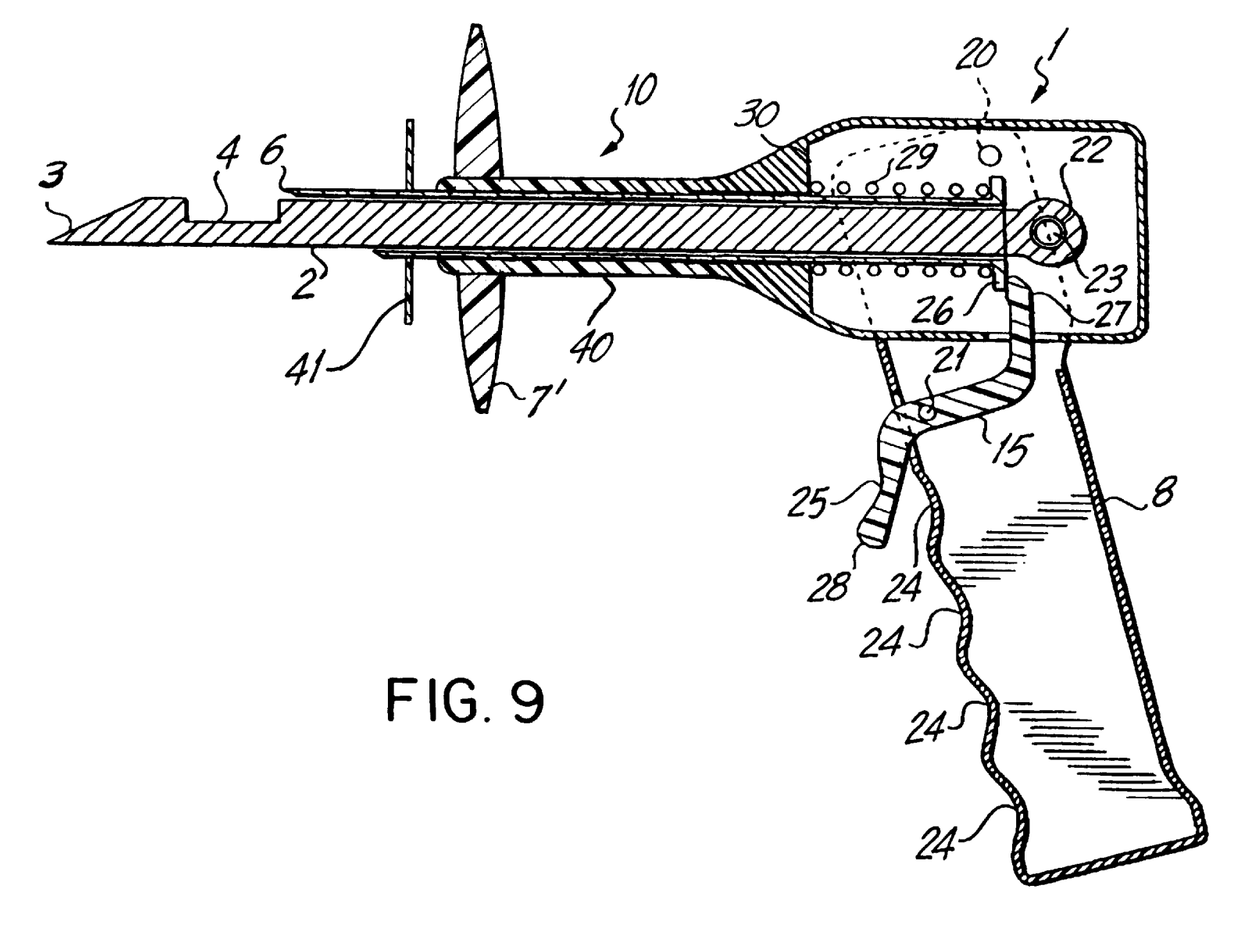
FIG. 9 shows a side cross-sectional view of another embodiment of the biopsy device of the invention taken along the central longitudinal axis of the needle.

In the embodiment of FIG. 9 the nose portion 40 of the housing 9 is extended and carries the transparent magnifying lens 7'. A separate disk 41, preferably also transparent, is carried on the sheath, and fastened thereto, and limits penetration of the sheath into the tissue. In this embodiment magnification is accomplished by the lens 7' and the disk 41 limits penetration into tissue.

Figure 10:
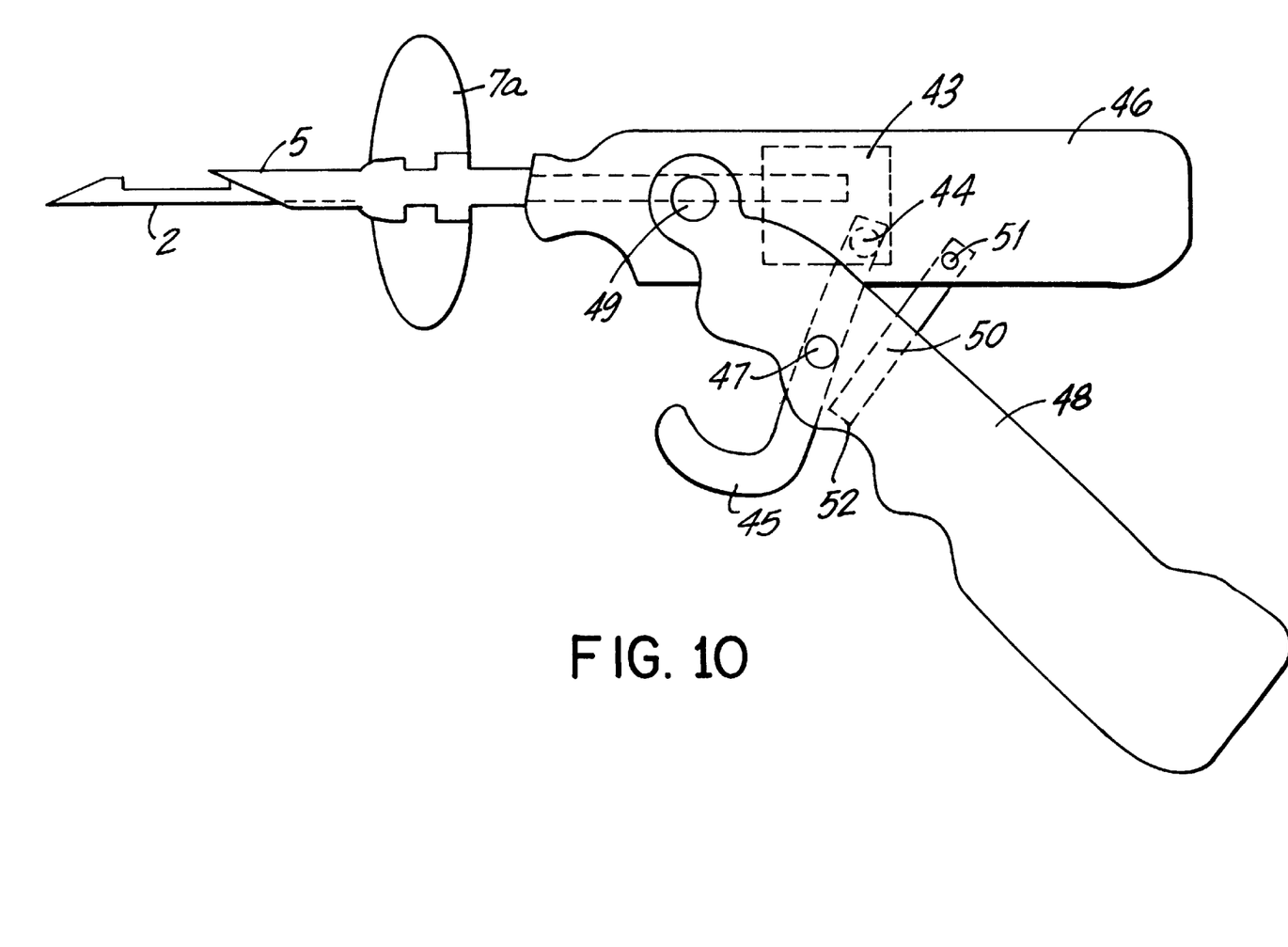
FIG. 10 shows a side view of another embodiment of the biopsy device.

In the embodiment of FIG. 10 the transparent magnifying lens 7a is carried on the sheath 5. A plate 43 is connected to the proximate end of the stylet 2. The lower end of plate 41 is pivotally attached, by pivot 44, near the top end of the trigger 45. The pivot 44 is held in the handle member 46.

Figure 11:
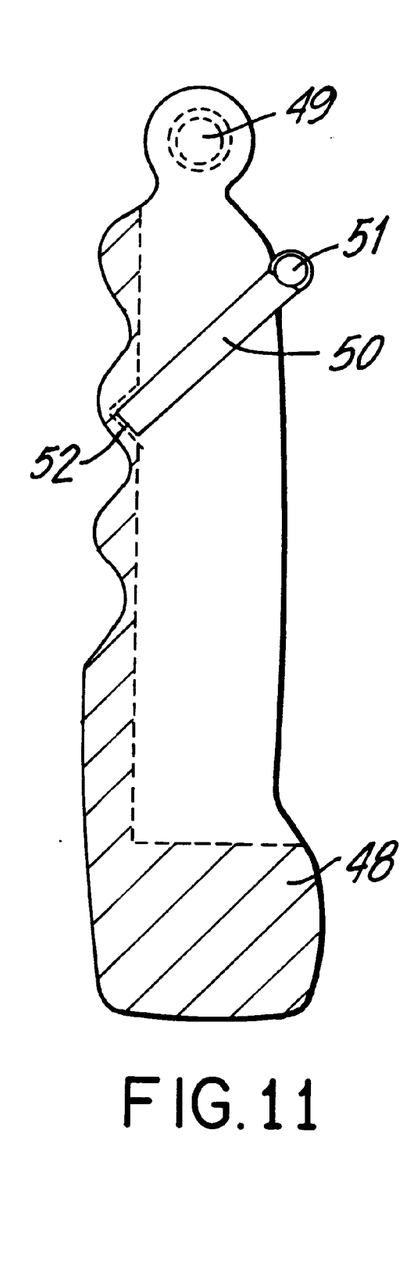
FIG. 11 is a partial view, in cross-section, of a handle portion of the device of FIG. 10.
Figure 12:
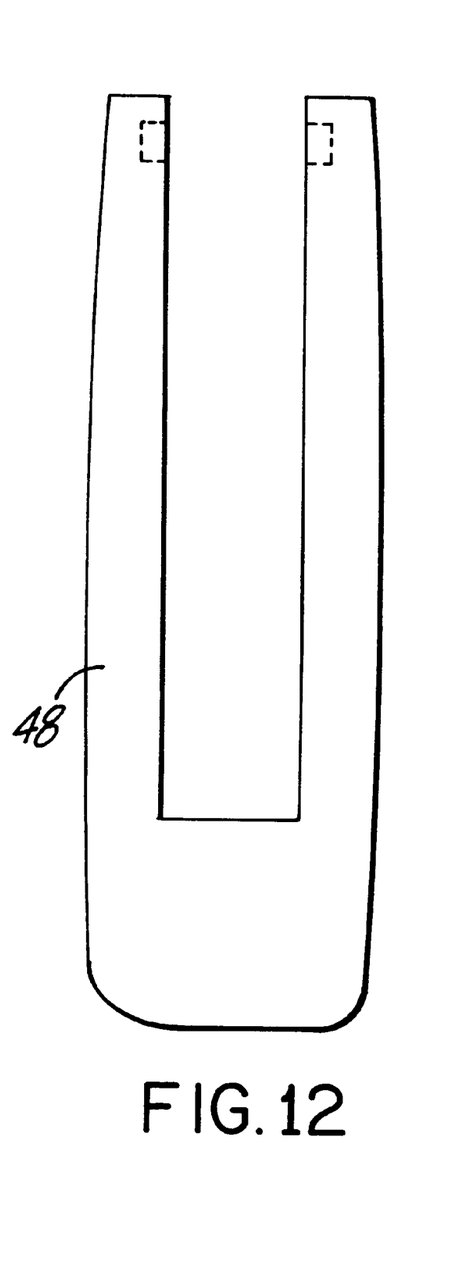
FIG. 12 is a front view of the handle portion of FIG. 11.

The trigger 45 pivots on pivot 47 which is held in handle member 48. The handle member 48 is pivotly attached to the handle member 46 by pivot 49, see FIG. 11. A strut 50, pivotly attached by pivot 51 to handle member 46, may be lodged in a cavity 52 in handle member 48 to space the handle members from each other.

Figure 13:
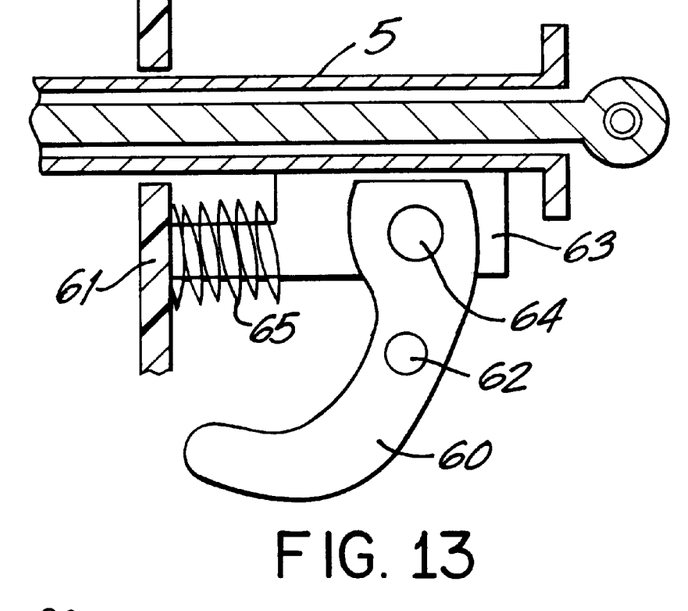
FIGS. 13 and 14 are side cross-sectional and enlarged views of alternative trigger mechanisms.
Figure 14:
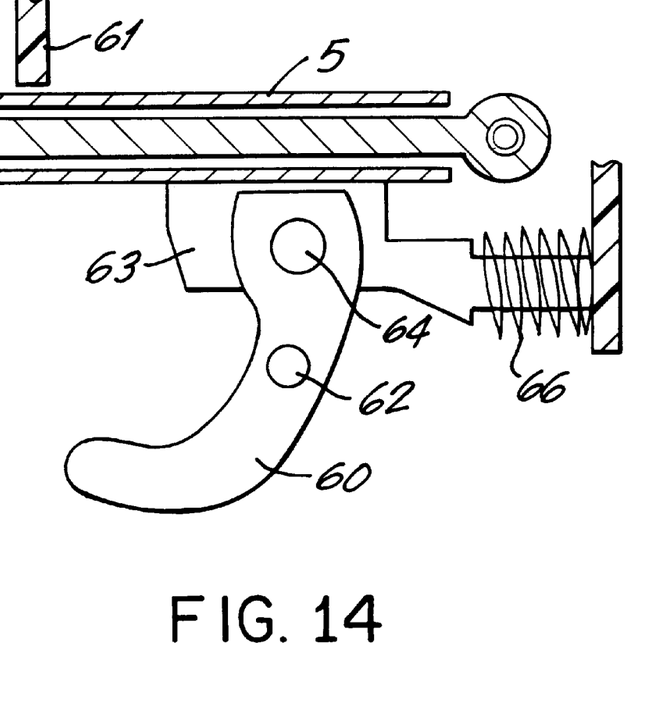

FIGS. 13 and 14 show alternative trigger mechanisms. In both FIGS. 13 and 14 a trigger 60 is pivotly attached to a housing 61 at pivot 62. The top of the trigger 60 is pivotly attached to plate 63 by pivot 64. The plate 63 is attached to the tubular sheath 5. When trigger 60 is pulled, i.e., its bottom rotated counter-clockwise in FIGS. 13 and 14, the sheath 5 is moved forward.

In the embodiment of FIG. 13 a spring 65 is compressed by pulling trigger 60 and returns the sheath to its normal (retracted) position when the trigger is released. That is the same operation as in the embodiment of FIG. 8.

In the embodiment of FIG. 14 a spring 66 is compressed when the trigger is pulled. Spring 66 returns the sheath to its normal position in which, in FIG. 14, it is advanced and covers the cradle 4. In this embodiment the trigger is pulled before the stylet is advanced into tissue. The trigger is then released and the sheath is advanced by the spring 66 to cut the tissue. The device is then removed and the trigger operated to remove cells from the cradle.

Figure 15:
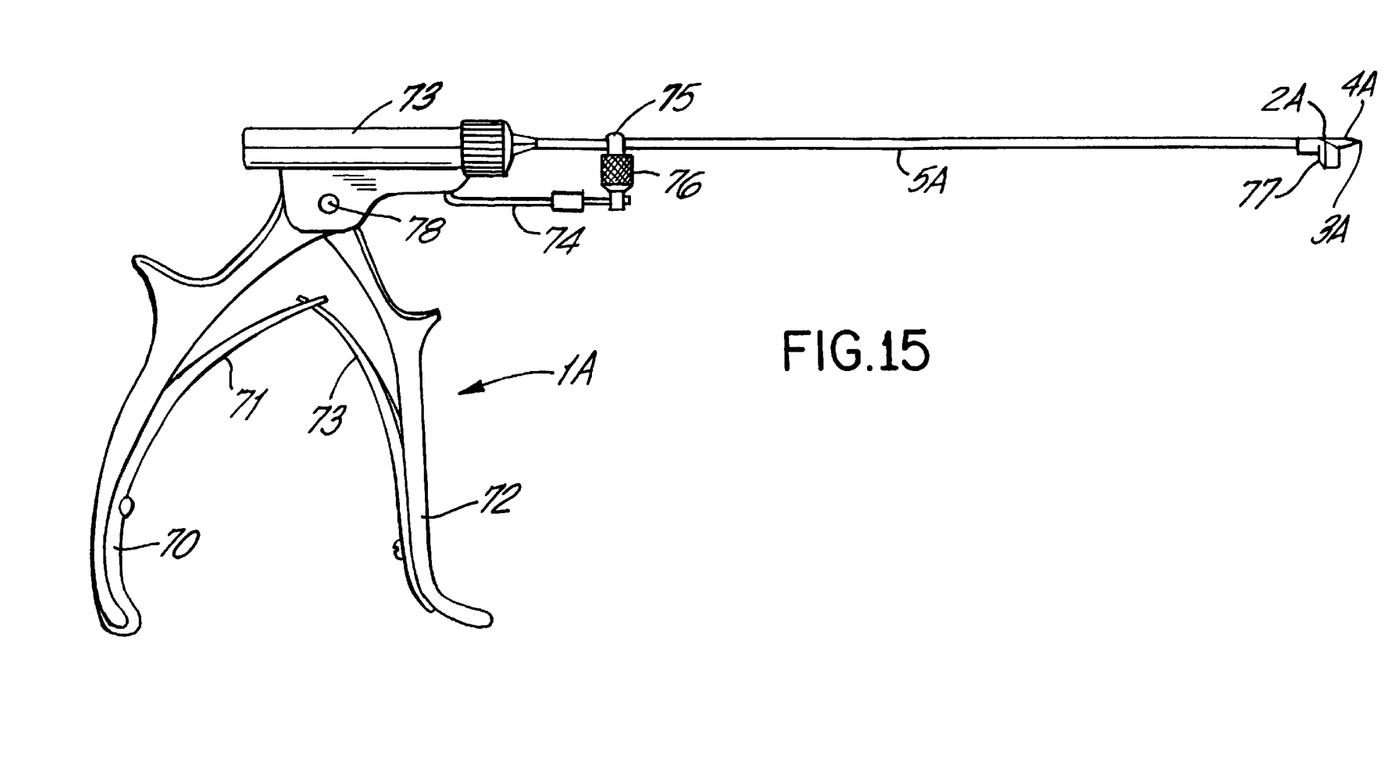
FIG. 15 is a side view of another embodiment of the biopsy device of the invention.

In the embodiment of FIG. 15 the needle is a rod which has a stylet 2A having a sharp tip 3A and a cradle 4A. A sheath 5A (tubular cannula) surrounds the needle. The handle 1A has a fixed arm 70 having a spring blade 71 and a pivotable trigger arm 72 having a second spring blade 73 which pivots on pin 78. The spring blades act to normally separate arm 70 from arm 72. The arm 72 is connected within body 73 to the sheath 5A. A rod 72 is fixed relative to the arm 70 and the needle. The rod 74 passes through a hole in shaft 75. The sheath 5A, to which shaft 75 is connected, may be held in position by tightening nut 76 on the external screw-threaded shaft 75. A disk 77 is fixed on the sheath 5A in the same position as the magnifying lens of the prior embodiments. The disk 77 is one-half of a round shape, i.e., semi-round (180° of complete round disk) and is of metal. It is a barrier to limit the depth of penetration of the sheath. The sheath and stylet operate in the same manner as in the prior embodiments, except there is no lens through which to view the cervix.

Although the invention has been described in considerable detail with respect to preferred embodiments thereof, variations and modifications will be apparent to those skilled in the art without departing from the spirit and scope of the invention as set forth in the claims.

What is claimed is:

1. A method of performing a cervical biopsy using a biopsy device comprising a needle attached to a handle, the needle comprising a stylet having a sharp tip thereon and a cradle, a sheath surrounding a portion of the stylet and movable with respect to the longitudinal axis thereof, the sheath having a cutting edge corresponding to the tip of the stylet, and a limiting barrier positioned and fixed on the sheath proximate the cutting edge, the handle including finger operated trigger means for moving the sheath on the stylet, the method comprising the steps of:

inserting the stylet and sheath into a wall of the cervix, until the barrier abuts an outer wall of the cervix, while viewing tissue surrounding the stylet;

finger operating said trigger and thereby moving the cutting edge in a direction of the tip to cut tissue and collect a tissue specimen in the cradle; and removing the needle from the cervix while keeping the sheath over the cradle to cover the tissue in the cradle.

* * * * *